United States Patent
Buchwald et al.

(10) Patent No.: US 11,419,516 B2
(45) Date of Patent: Aug. 23, 2022

(54) MRI SYSTEM COMPRISING PATIENT MOTION SENSOR

(71) Applicant: GE Precision Healthcare LLC, Wauwatosa, WI (US)

(72) Inventors: Randall H. Buchwald, Nashotah, WI (US); Louis Jay Vannatta, Crystal Lake, IL (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 479 days.

(21) Appl. No.: 16/551,011

(22) Filed: Aug. 26, 2019

(65) Prior Publication Data
US 2021/0059555 A1 Mar. 4, 2021

(51) Int. Cl.
| | |
|---|---|
| A61B 5/05 | (2021.01) |
| A61B 5/055 | (2006.01) |
| A61B 5/11 | (2006.01) |
| A61B 5/113 | (2006.01) |
| G01R 33/341 | (2006.01) |
| G01R 33/567 | (2006.01) |
| G01R 33/36 | (2006.01) |

(52) U.S. Cl.
CPC ............ *A61B 5/055* (2013.01); *A61B 5/113* (2013.01); *A61B 5/1114* (2013.01); *G01R 33/341* (2013.01); *G01R 33/3692* (2013.01); *G01R 33/5676* (2013.01)

(58) Field of Classification Search
CPC ....... A61B 5/055; A61B 5/1114; A61B 5/113; G01R 33/3692; G01R 33/341; G01R 33/5676
See application file for complete search history.

(56) References Cited

U.S. PATENT DOCUMENTS

| | | | |
|---|---|---|---|
| 4,712,560 A | 12/1987 | Schaefer et al. | |
| 2009/0256569 A1* | 10/2009 | Hancu | G01R 33/34076 324/322 |
| 2013/0069843 A1* | 3/2013 | Singh | H01Q 1/38 343/866 |
| 2013/0165768 A1* | 6/2013 | Biber | G01R 33/3664 600/422 |
| 2016/0209486 A1* | 7/2016 | Nisznansky | G01R 33/56509 |

* cited by examiner

*Primary Examiner* — Joel F Brutus
(74) *Attorney, Agent, or Firm* — Andrus Intellectual Property Law, LLP

(57) ABSTRACT

A table for an MRI system includes a top surface for supporting a patient being imaged and a motion sensor for sensing motion of the patient. The motion sensor is located below the top surface and includes a self-resonant spiral (SRS) coil and a coupling loop. The coupling loop generates a drive RF signal to excite the SRS coil to radiate a magnetic field having a predefined resonant frequency. The coupling loop also receives a reflection RF signal from the SRS coil. The motion sensor is located such that at least a portion of a torso of the patient being imaged is within the magnetic field. A controller is configured to detect patient motion based on the reflection RF signal.

22 Claims, 8 Drawing Sheets

MRI SYSTEM COMPRISING PATIENT MOTION SENSOR

BACKGROUND

The present disclosure generally relates to magnetic resonance imaging (MRI) and, more particularly, to an MRI system having a contactless motion sensor for detecting patient motion, including motion of the patient due to respiration.

Magnetic resonance (MR) imaging is often used to obtain internal physiological information of a patient, including for cardiac imaging and imaging other sections or tissues within a patient's torso (or anywhere on the patient). In certain body areas, such as portions in the torso, it is typically desirable to obtain an image at a particular point in a variable cycle (e.g. respiratory cycle and/or cardiac cycle), such as a peak of the variable cycle, to analyze behavior during that peak. Gating is an option for characterizing different attributes of an organ for imaging. The most common techniques of gating include cardiac, respiratory, and peripheral pulse gating, and these types of gating have uses in numerous medical applications across diagnostic modalities such as CT, MR, x-ray, ultrasound, and position emission tomography (PET). Respiratory gating, for example, is an essential component of cardiac imaging while using imaging modalities such as CT and MR to minimize motion-related artifacts resulting from motion due to the patient's respiration.

In MR imaging, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", Mz, may be rotated, or "tipped", into the x-y plane to produce a net transverse magnetic moment Mt. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using reconstruction techniques.

For example, MR images of the cardiac region or abdominal region are often used by health care professionals to diagnose medical conditions. Traditional MR evaluations of the cardiac or abdominal regions often rely on repeated cardiac-gated and/or respiratory-gated acquisition of MR data in order to reduce image degradation resulting from the continuous movement of the imaged tissues due to respiratory and/or circulatory physiological functions.

Accordingly, respiratory gating and/or cardiac gating are often used in acquisition of MR data, which rely on detection of a particular point in the motion cycle as a trigger to repeatedly acquire data at approximately the same phase of the motion cycle. Sensor systems are utilized to sense respiration activity and cardiac potentials. Respiratory monitors utilizing bellows sensors are often employed for detecting respiratory wave forms, which detect chest expansion utilizing a belt and bellows comprising a pressure sensor. An electrocardiogram (ECG) is generally utilized to monitor the cardiac cycle.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a table for an MRI system includes a top surface for supporting a patient being imaged and a motion sensor for sensing motion of the patient. The motion sensor is located below the top surface and includes a self-resonant spiral (SRS) coil excited by a drive signal to radiate a magnetic field having a predefined resonant frequency. A driver-receiver is coupled to the SRS coil and configured to generate the drive signal to excite the SRS coil and to receive an RF signal from the SRS coil. The motion sensor is located such that at least a portion of a torso of the patient being imaged is within the magnetic field. A controller is configured to detect patient motion based on the reflection RF signal.

An MRI system includes a bore, a table configured to support a patient being imaged and moveable to move the patient in and out of the bore, and a motion sensor for sensing motion of the patient during imaging. The motion sensor includes a self-resonant spiral (SRS) coil and a coupling loop inductively coupled to the SRS coil and configured to generate a drive RF signal to excite the SRS coil and receive a reflection RF signal from the SRS coil. The motion sensor is located such that at least a portion of the patient's torso is within the magnetic field while the patient is being imaged in the bore. A controller is configured to detect a patient motion based on changes in the reflection RF signal.

Another embodiment of an MRI system includes a bore, a table having a top surface that supports a patient being imaged and moveable to move the patient in and out of the bore, and a motion sensor located below the top surface of the table and configured to sense motion of the patient due to respiration. The motion sensor system includes a first resonant coil positioned toward a front end of the table and a first coupling loop coupled to the first resonant coil, wherein the first coupling loop is configured to generate a drive RF signal to excite the first resonant coil to radiate a magnetic field having a predefined frequency. The first coupling loop also receives a reflection RF signal from the first resonant coil. The motion sensor system further includes a second resonant coil positioned toward a back end of the table and a second coupling loop coupled to the second resonant coil. The second coupling loop is configured to generate a drive RF signal to excite the second resonant coil to radiate a magnetic field having the predefined resonant frequency. The second coupling loop is also configured to receive a reflection RF signal from the second resonant coil. A switch is configured to alternately connect one of the first coupling loop and the second coupling loop to a controller. The controller is configured to generate a respiratory signal based on changes in the reflection RF signal due to respiration.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
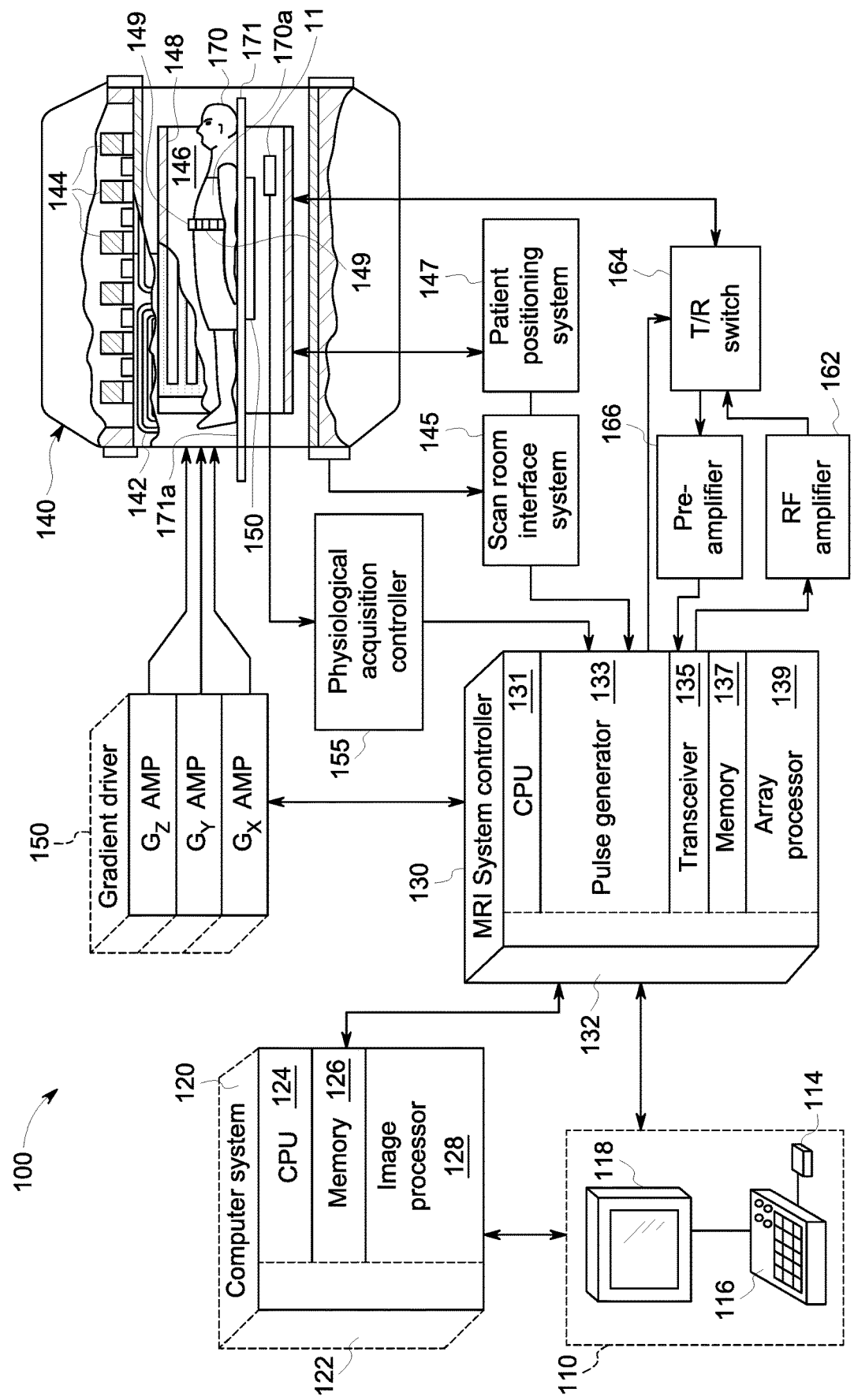
FIG. 1 is a schematic diagram of an exemplary MRI system in accordance with one embodiment of the present disclosure.

Accurate respiratory parameter measurement is important for respiratory gating in MR imaging. The inventors have recognized the need for an improved respiration monitoring system for utilization in MR imaging, such as for generating a respiration signal. The inventors have recognized that traditional bellows respiration sensors are undesirable because they can be uncomfortable for the patient and require additional clinician time to place the belt and bellows sensor on the patient prior to imaging.

The inventors have recognized a need for a reliable contactless respiration sensor that is integrated into an MRI system and operates without needing to attach any sensors to a patient and without requiring any additional setup or engagement by a clinician conducting MR imaging. Accordingly, the inventors have developed the disclosed motion sensor system configured to detect respiratory motion of a patient, and may be configured to detect other types of patient motion as well. The motion sensor system includes a resonant coil and a driver-receiver, such as a coupling loop inductively coupled to the resonant coil. In one embodiment, the coupling loop is configured to generate a drive RF signal to excite the resonant coil to radiate a magnetic field having a predefined resonant frequency, and the coupling loop also receives a reflection RF from the resonant coil. Based on the reflection RF signal, a respiration signal can be derived. For example, the respiration signal may be determined based on changes in a reflection coefficient (S11) of the resonant coil over time. In other embodiments, differing drive methods may be utilized, such as via a direct connection. In a direct drive embodiment, the resonant coil is directly driven via connection to a voltage source and the sensing of S11 is accomplished through the same direct drive connection. There, the driver-receiver physically connects to one end of the coil, such as at the center.

The inventors have recognized that prior art contactless motion detection systems utilizing HF resonators are unreliable to detecting patient respiration due to small region of sensitivity and small magnetic fields utilized. Moreover, prior art respiration systems are not integrated into MR imaging systems, such as integrated into the table, and thus may require positioning and/or other involvement of a clinician, in order to set up the motion sensing system for a patient being imaged, particularly for heavier patients or patients with abnormal breathing styles (chest versus belly breathers), and/or existing systems require use of specialized receiver coils that incorporated and design around the contactless motion sensor systems.

In view of the foregoing challenges in the relevant art, the inventors developed the disclosed system that generates an RF magnetic field having a greater depth of penetration and a larger region of sensitivity than prior art systems. In one embodiment, the motion sensor system includes one or more sensors integrated into a table of the MR system and generating a magnetic field of sufficient magnitude to reliably measure patient respiration during MR imaging. For example, the contactless sensors may be configured such that they can reliably measure patient respiration from a measuring distance of around 4-6 inches between the patient and the sensor coil, embodiments of which are thoroughly described herein. The sensors may be located at various positions on the table and may be selectable depending on the patient's position on the table (i.e. head-first or feet-first) and/or the type of imaging being performed.

Referring to FIG. 1, a schematic diagram of an exemplary MRI system 100 is shown in accordance with an embodiment. The operation of MRI system 100 is controlled from an operator workstation 110 that includes an input device 114, a control panel 116, and a display 118. The input device 114 may be a joystick, keyboard, mouse, track ball, touch activated screen, voice control, or any similar or equivalent input device. The control panel 116 may include a keyboard, touch activated screen, voice control, buttons, sliders, or any similar or equivalent control device. The operator workstation 110 is coupled to and communicates with a computer system 120 that enables an operator to control the production and viewing of images on display 118. The computer system 120 includes a plurality of components that communicate with each other via electrical and/or data connections 122. The computer system connections 122 may be direct wired connections, fiber optic connections, wireless communication links, or the like. The components of the computer system 120 include a central processing unit (CPU) 124, a memory 126, which may include a frame buffer for storing image data, and an image processor 128. In an alternative embodiment, the image processor 128 may be replaced by image processing functionality implemented in the CPU 124. The computer system 120 may be connected to archival media devices, permanent or back-up memory storage, or a network. The computer system 120 is coupled to and communicates with a separate MRI system controller 130.

The MRI system controller 130 includes a set of components in communication with each other via electrical and/or data connections 132. The MRI system controller connections 132 may be direct wired connections, fiber optic connections, wireless communication links, or the like. The components of the MRI system controller 130 include a CPU 131, a pulse generator 133, which is coupled to and communicates with the operator workstation 110, a transceiver 135, a memory 137, and an array processor 139. In an alternative embodiment, the pulse generator 133 may be integrated into a resonance assembly 140 of the MRI system 100. The MRI system controller 130 is coupled to and receives commands from the operator workstation 110 to indicate the MRI scan sequence to be performed during a MRI scan. The MRI system controller 130 is also coupled to and communicates with a gradient driver system 150, which is coupled to a gradient coil assembly 142 to produce magnetic field gradients during a MRI scan.

The pulse generator 133 may also receive data from a physiological acquisition controller 155 that receives signals from a plurality of different sensors connected to an object or patient 170 undergoing a MRI scan, including respiration signals and/or cardiac signals (e.g., ECG signals). And finally, the pulse generator 133 is coupled to and communicates with a scan room interface system 145, which receives signals from various sensors associated with the condition of the resonance assembly 140. The scan room interface system 145 is also coupled to and communicates with a patient positioning system 147, which sends and receives signals to control movement of a table 171. The able 171 is controllable to move the patient in and out of the bore 146 and to move the patient to a desired position within the bore 146 for a MRI scan.

The MRI system controller 130 provides gradient waveforms to the gradient driver system 150, which includes, among others, $G_X$, $G_Y$ and $G_Z$ amplifiers. Each $G_X$, $G_Y$ and $G_Z$ gradient amplifier excites a corresponding gradient coil in the gradient coil assembly 142 to produce magnetic field gradients used for spatially encoding MR signals during a MRI scan. The gradient coil assembly 142 is included within the resonance assembly 140, which also includes a superconducting magnet having superconducting coils 144, which in operation, provides a homogenous longitudinal magnetic field $B_0$ throughout a bore 146, or open cylindrical imaging volume, that is enclosed by the resonance assembly 140. The resonance assembly 140 also includes a RF body coil 148 which in operation, provides a transverse magnetic field $B_1$ that is generally perpendicular to $B_0$ throughout the bore 146. The resonance assembly 140 may also include RF surface coils 149 used for imaging different anatomies of a patient undergoing a MRI scan. The RF body coil 148 and RF surface coils 149 may be configured to operate in a transmit and receive mode, transmit mode, or receive mode.

An object or patient 170 undergoing a MRI scan may be positioned within the bore 146 of the resonance assembly 140. The transceiver 135 in the MRI system controller 130 produces RF excitation pulses that are amplified by an RF amplifier 162 and provided to the RF body coil 148 and RF surface coils 149 through a transmit/receive switch (T/R switch) 164.

As mentioned above, RF body coil 148 and RF surface coils 149, and/or one or more phased-array (PA) coils 150, may be used to transmit RF excitation pulses and/or to receive resulting MR signals from a patient undergoing a MRI scan. For example, the PA coil(s) 150 may be located in the table underneath the patient 170, such as in an area under the torso 170a of the patient. The resulting MR signals emitted by excited nuclei in the patient undergoing a MRI scan may be sensed and received by the RF body coil 148, RF surface coils 149, or PA coil 150. Each of the coils 148, 149, and 150 usually include a respective T/R switch, and each usually include the T/R function and preamps within the surface coil/PA coil itself. Thus multiple T/R switches are included in the system, which are collectively represented as T/R switch 164. Similarly, multiple preamps may be included, which are collectively represented as preamplifier 166. The amplified MR signals are demodulated, filtered and digitized in the receiver section of the transceiver 135. The appropriate T/R switch 164 is controlled by a signal from the pulse generator 133 to electrically connect the amplifier 162 to the appropriate coil 148, 149, 150 during the transmit mode and connect the corresponding preamplifier 166 to the coil 148, 149, 150 during the receive mode. The resulting MR signals sensed and received by the RF body coil 148 or the PA coil 150 are digitized by the transceiver 135 and transferred to the memory 137 in the MRI system controller 130.

A MR scan is complete when an array of raw k-space data, corresponding to the received MR signals, has been acquired and stored temporarily in the memory 137 until the data is subsequently transformed to create images. This raw k-space data is rearranged into separate k-space data arrays for each image to be reconstructed, and each of these separate k-space data arrays is input to the array processor 139, which operates to Fourier transform the data into arrays of image data.

The array processor 139 uses a known transformation method, most commonly a Fourier transform, to create images from the received MR signals. These images are communicated to the computer system 120 where they are stored in memory 126. In response to commands received from the operator workstation 110, the image data may be archived in long-term storage or it may be further processed by the image processor 128 and conveyed to the operator workstation 110 for presentation on the display 118. In various embodiments, the components of computer system 120 and MRI system controller 130 may be implemented on the same computer system or a plurality of computer systems.

A motion sensor 11 is integrated into the resonance assembly 140 to sense motion of the patient. The detected motion information can be utilized for controlling and optimizing imaging, such as for aiding the MR image capture based on detected periodic motion and/or otherwise improving image quality by avoiding image degradation due to patient motion. The motion sensor 11 generates a magnetic field by which motion of the patient can be detected, as described herein below. The motion information is provided to the physiological acquisition controller (PAC) 155, which provides information about the periodic and/or other motion of the patient to the pulse generator 133. For example, the PAC controller 155 may generate a respiration signal formatted for use in triggering MR image data acquisition performed by the MRI system controller 130.

Figure 2:
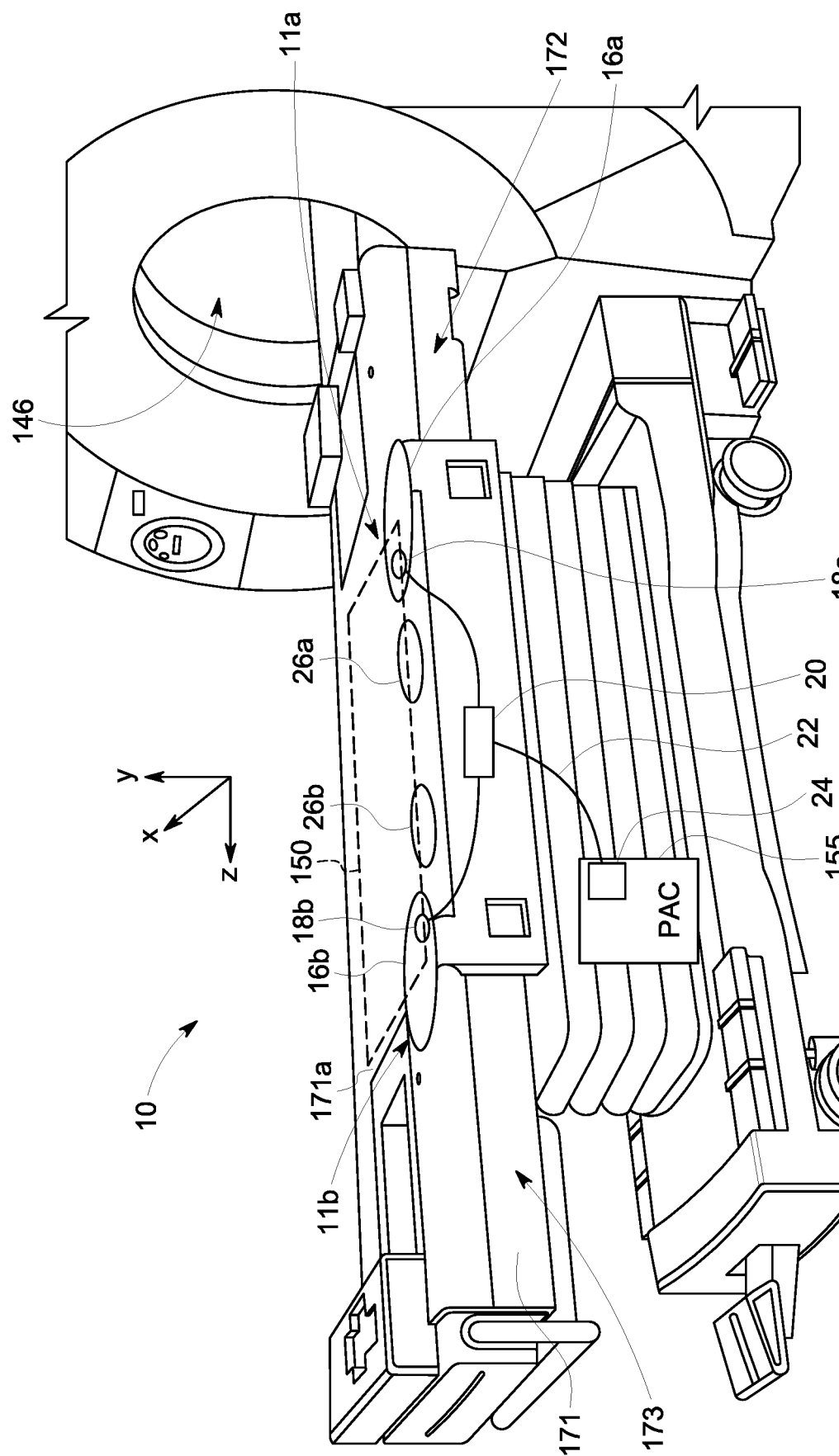
FIG. 2 depicts an exemplary table of an MRI system according to another embodiment of the present disclosure.

Referring to FIG. 2, a table 171 is shown schematically illustrating an exemplary motion sensor system 10 incorporated therein. The table 171 is outside of the bore 146 and is moveable into the bore 146 in order to conduct patient imaging. The table 171 has a top surface 171a for supporting the patient 170 being imaged. In the depicted example, the table includes a PA coil 150 positioned below the top surface 171a. In the depicted example, two motion sensors 11a and 11b are located below the PA coil and are configured to sense motion of the patient. In other embodiments, the motion sensor 11a, 11b may be located elsewhere in the system 140, such as directly below the top surface 171a or elsewhere with respect to the patient, such as on the sides or above the patient in the bore 146.

Each motion sensor 11a, 11b includes a resonant coil 16a, 16b and a corresponding coupling loop 18a, 18b. Each coupling loop 18a, 18b is configured to generate a drive RF signal to excite the corresponding resonant coil 16a, 16b to radiate a magnetic field having a predefined resonant frequency. The coupling loop 18a, 18b is further configured to receive a reflection RF signal from the corresponding resonant coil 16a, 16b. In other embodiments, differing drive methods may be utilized, such as via a directly connected driver/receiver. In the case of a direct drive configuration, the sensing of S11 would also be accomplished through the direct drive connection. In one such embodiment, the SRS coil 36 may consist of two spiral elements interleaved with one rotated 180 degrees from the other. Each interleaved spiral element has a center end and an outer end. The ends closest to the center of the coil 36 may be driven directly using a voltage source in order to excite the SRS coil to generate the magnetic field. The receipt of the RF signal and sensing of S11 therefrom would also be accomplished through the direct connection. Thus, a coupling loop may be eliminated in a direct drive embodiment.

Each motion sensor 11a, 11b is located such that a relevant portion of the patient 170 is within a region of strong magnetic field with respect to the sensor 11a, 11b. Where respiration motion is being detected by the motion sensor 11a, 11b, the motion sensor 11a, 11b is positioned such that at least a portion of the torso 170a of the patient 170 is within an area of sufficiently strong magnetic field such that the motion of the torso 170a due to respiration can be detected. Time-varying loading of the magnetic field, the H-field, caused by the changes in absorption of the patient's tissue within the field can be measured and correspond to the respiratory cycle.

In one embodiment, this change is detected by measuring the reflection coefficient (S11) of the RF source power emitted by the coupling loop 18a, 18b into the resonant coil 16a, 16b. The reflection coefficient S11 represents how much power is reflected from the resonant coil 16a, 16b, which will be impacted by the changes in absorption by the patient due to respiration. Accordingly, a respiration signal can be determined based on changes in the reflection coefficient over a respiration period.

In the embodiment at FIG. 2, two motion sensors 11a, 11b are included. In other embodiments, only one motion sensor 11 may be included, or more than two motion sensors 11 may be included. One or more of the motion sensors 11a, 11b are selectable via a switch 20. In the depicted example, only one of the motion sensors 11a or 11b are selectable by connecting the respective coupling loop 18a, 18b to the controller, which in the example is the PAC controller 155. The appropriate motion sensor 11a or 11b is selected based on the direction of the patient for imaging—i.e. whether the patient is positioned head-first or feet-first for moving into the bore 146. In the example, motion sensor 11a is positioned closer to the front end 172 of the table 171 (the end that enters the bore first) and the motion sensor 11b is positioned closer to the back end 173 of the table 171 (the end that enters the bore last). The motion sensor 11a will be utilized if the patient is positioned head-first, where the patient's head is at the front end 172 of the table 171. Specifically, the motion sensor 11a is located so that it will align with the patient's torso 170a when the patient is positioned head-first toward the bore 146. Alternatively, if the patient is positioned feet-first toward the bore 146, then the motion sensor 11b may be selected via the switch 20, which is located to align with the patient's torso 170a when the patient is in the feet-first position.

In one example, selection of the appropriate motion sensor 11a or 11b by the switch 20 may be controlled based on whether the patient 170 to be imaged is positioned head-first or feet-first. The patient position is known, for example, by the MRI system controller 130 and is a parameter used for multiple control purposes within the MRI system 100. In one embodiment, actuation of the switch 20 to control selection of the motion sensor 11a or 11b may be performed by providing a pre-defined DC bias on the drive signal coax cable, where a different pre-defined DC bias is associated with each motion sensor 11a and 11b.

The motion sensors 11a and 11b are connected to the controller 155, such as via a coax cable 22. In one example, the controller 155 is a PAC controller 155 comprising a respiration detection sub-controller 24 that includes circuitry for filtering and digitizing the analog reflectometer measurement provided by the motion sensor 11a, 11b and software for processing the digitized signal in order to generate a respiration signal that can be utilized for controlling MR image acquisition.

Figure 3:
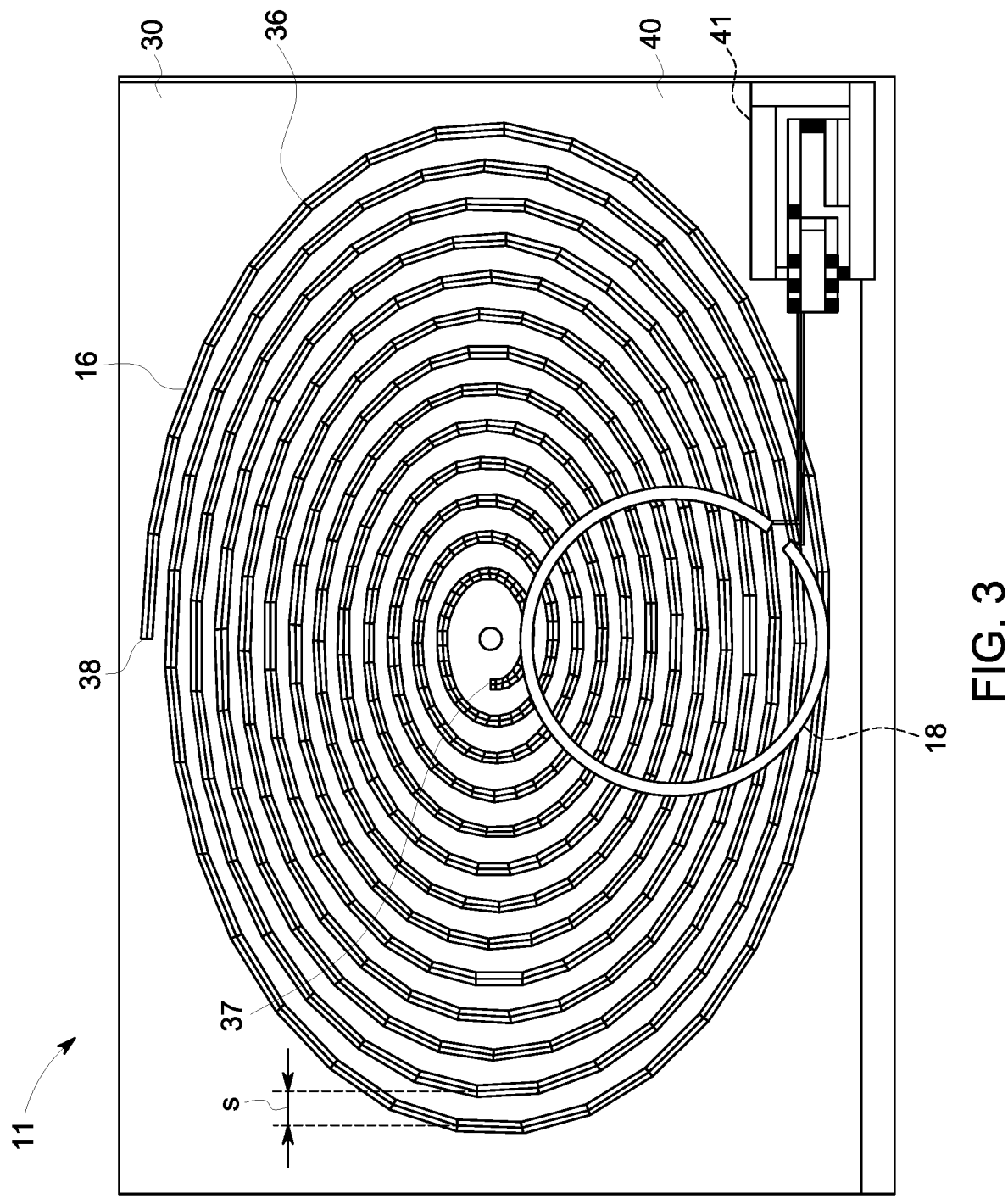
FIG. 3 depicts one embodiment of a motion sensor according to one embodiment of the present disclosure.

FIGS. 3-5A and 5B, and 7 depict exemplary embodiments of a motion sensor 11. FIG. 3 depicts an embodiment where the resonant coil 16 is a self-resonant spiral (SRS) coil 36. In other embodiments, the resonant coil 16 may instead by a circular coil or an air coil located at closer proximity to the posterior of the patient 170. In one embodiment, the self-resonant spiral provides for a larger H-field generation due to its multi-turn nature with the tuning capacitance dominated by the distributed capacitance between turns of the spiral. This allows the SRS coil 36 to be located further away from the patient than other types of resonant coils, while still providing useful detection of the patient loading of the field that is sufficiently sensitive to provide good detection of patient respiration, for example. The SRS coil 36 with multiple turns is driven at a frequency below that of the proton scanning, or Larmor frequency, to produce a strong H-field with a large depth of penetration into the scanner subject that will not create interference with the MR imaging.

Figure 7:
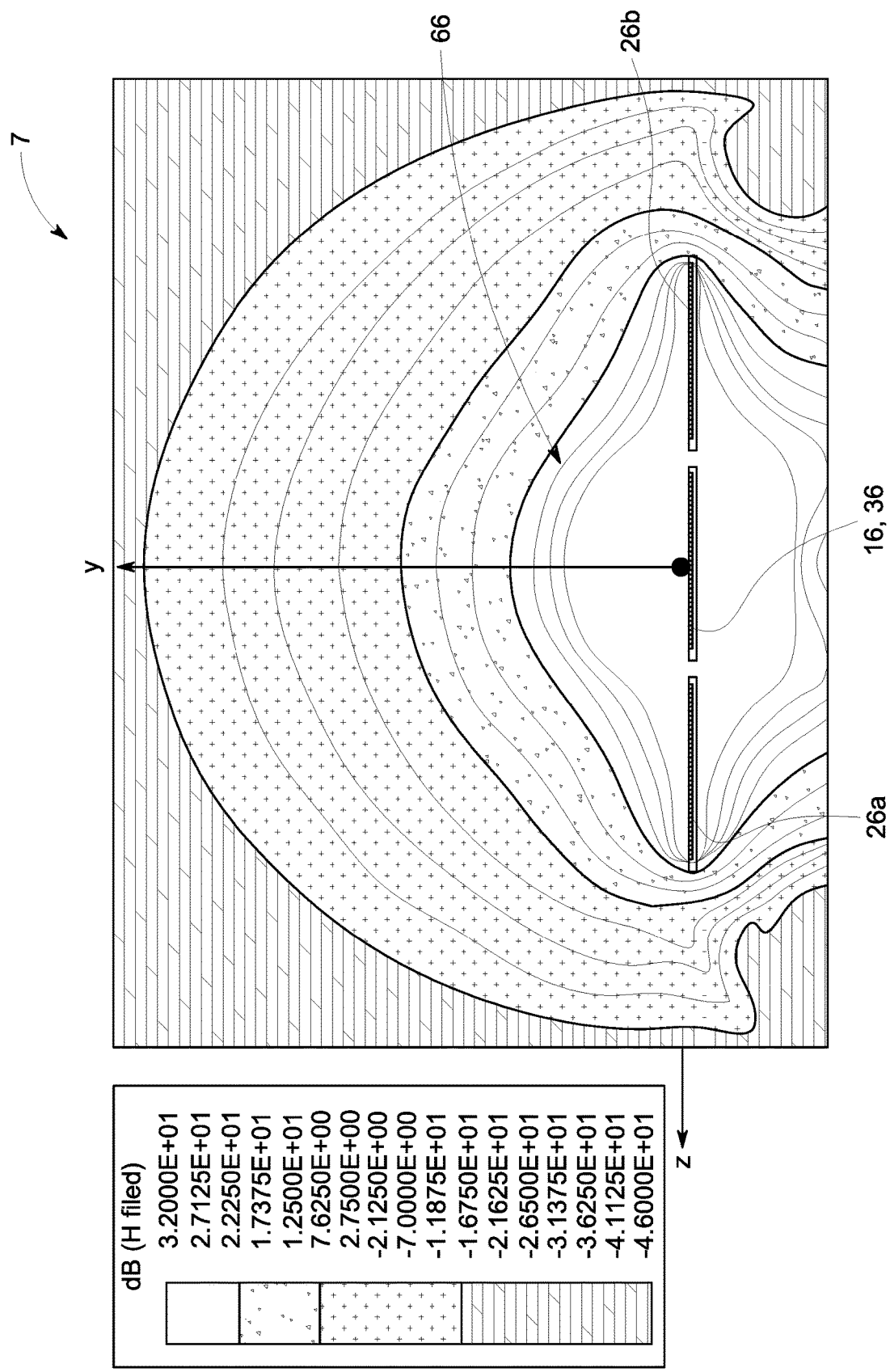
FIG. 7 is an H-field diagram of a magnetic field radiated by exemplary resonant coil and two passively coupled elements according to one embodiment of the present disclosure.

Referencing FIG. 7 in particular, when excited by the drive RF signal generated by the coupling loop, the SRS coil 36 has a low source impedance, with the H-field dominating the near field environment. The depth of the near field 66, in meters, is approximated by the following equation:

$$\text{Depth} = \frac{150}{2\pi f(\text{MHz})}$$

The field is attenuated at a rate of 1/r3, where r is the distance from the source normalized to $\lambda/2\pi$. As explained in more detail below, the RF magnetic field will have a greater depth of penetration when the source frequency is lower.

FIG. 3 depicts one embodiment of an SRS coil 36. The exemplary SRS coil 36 includes 13 turns between a first end 37 and a second end 38 of the conductor, or wire, comprising the coil. In the example, the circular coils are consistently spaced apart, with spacing S being another parameter affecting the resonance frequency and the magnitude of the H-field. In other examples, and depending on the application, a different number of turns and/or different spacing may be utilized, and the spacing may vary depending on the shape of the SRS coil 36. For an elliptical coil, for example, the spacing will vary as a function of the angle of rotation around the center of the coil and as a function of the eccentricity of the ellipse. For instance, the inventors have recognized that various numbers of turns, such as between 10 and 15 turns, may be appropriate depending on the desired resonance frequency and the needed H-field magnitude, which may depend on placement within the table, for example. In the example at FIG. 3, the SRS coil 36 is elliptical. In other embodiments, a differing shape may be used. FIG. 5B depicts another example showing exemplary dimensions of an elliptical SRS coil 36. An elliptical self-resonant spiral coil will generate a stronger magnetic field for a given excitation current. Moreover, the elliptical coil may have the added benefit that it will fit in a narrower space, which may be beneficial for fitting the sensor 11 into the crowded space of the table 171.

The coupling loop 18 is inductively coupled to the SRS coil 36, or other resonant coil 16. The coupling loop 18 is configured to generate a drive RF signal to excite the SRS coil to radiate a magnetic field at a predefined frequency. In one embodiment, the use of a 27 MHz SRS coil 36 is desirable in that it provides for a large H-field generation due to its multi-turn nature with the tuning capacitance dominated by the distributed capacitance between the turns of the spiral. 27 MHz is beneficially within an Industrial, Scientific, and Medical (ISM) band. In other embodiments, a different predefined resonant frequency may be utilized, which may be a different ISM band frequency. To provide one example, the predefined resonant frequency may be in the ISM band between 26.975 MHz and 27.283 MHz, or may be between 40.66 MHz and 40.7 MHz, or in still other embodiments may be between 13.553 MHz and 13.567 MHz. In other embodiments, the predetermined resonant frequency may be different and/or outside of those ISM bands. In certain examples, it may be beneficial to utilize a predetermined resonant frequency that is below that of the proton scanning frequency.

The coupling loop 18 also receives a reflection RF signal from the SRS coil 36 such that a respiratory, or other patient motion, signal can be detected by measurement of the change in the reflection RF signal due to the variation in loading that the patient presents to this RF H-field. As the patient breathes, for example, the amount of power reflected by the SRS coil 36 will change. In one embodiment, the motion signal, such as the respiration signal, is determined based on a reflection coefficient S11 of the SRS coil 36. In the depicted embodiment at FIG. 4, a dual log power detection integrated circuit is used in combination with directional couplers to measure the reflected power, the reflection RF signal, divided by the forward power, the drive RF signal, delivered at 27 MHz. The reflection coefficient S11 can then be calculated according to the following equation:

$$S11 = \log 10(P_{refl}) - \log 10(P_{drv})$$

Figure 4:
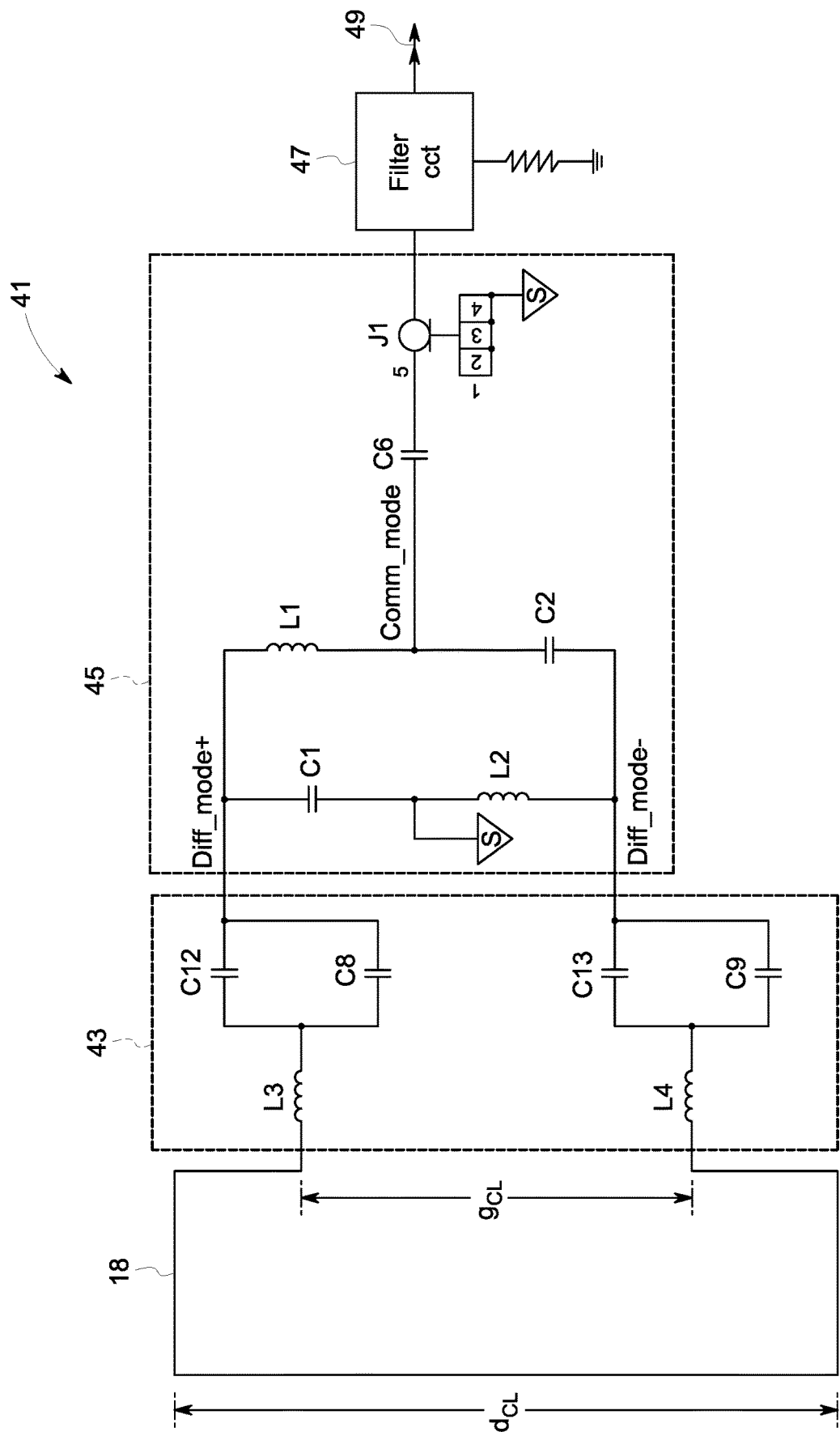
FIG. 4 is a circuit diagram of an exemplary coupling circuit of a motion sensor according to one embodiment of the present disclosure.

FIG. 4 depicts one embodiment of a coupling board 40, including the coupling loop and the coupling circuit 41 for detecting the patient motion based on changes in the reflection RF signal. The coupling loop 18 is, for example, a circular loop of a specified diameter $d_{cl}$. To provide just one example, the diameter $d_{cl}$ of the coupling loop 18 may be 50 mm, and the gap $g_{cl}$ between the ends of the coupling loop 18 may be, for example, 5 mm. The coupling circuit 41 includes a blocking network 43 that blocks other resonant frequencies other than those at 27 MHz, or the predefined resonant frequency. A lattice balun circuit 45 is further included that translates a differential output of the loop to a single-ended coax feed line. The lattice balun is effective at desensitizing the sensor assembly to frequency shifts. A filtering circuit 47, such as a diplexer, is further included to filter the outputted reflectometer measurement signal prior to transmission to the controller 155. The resulting signal is provided to the socket 49 such as a coax connector.

Figure 5A:
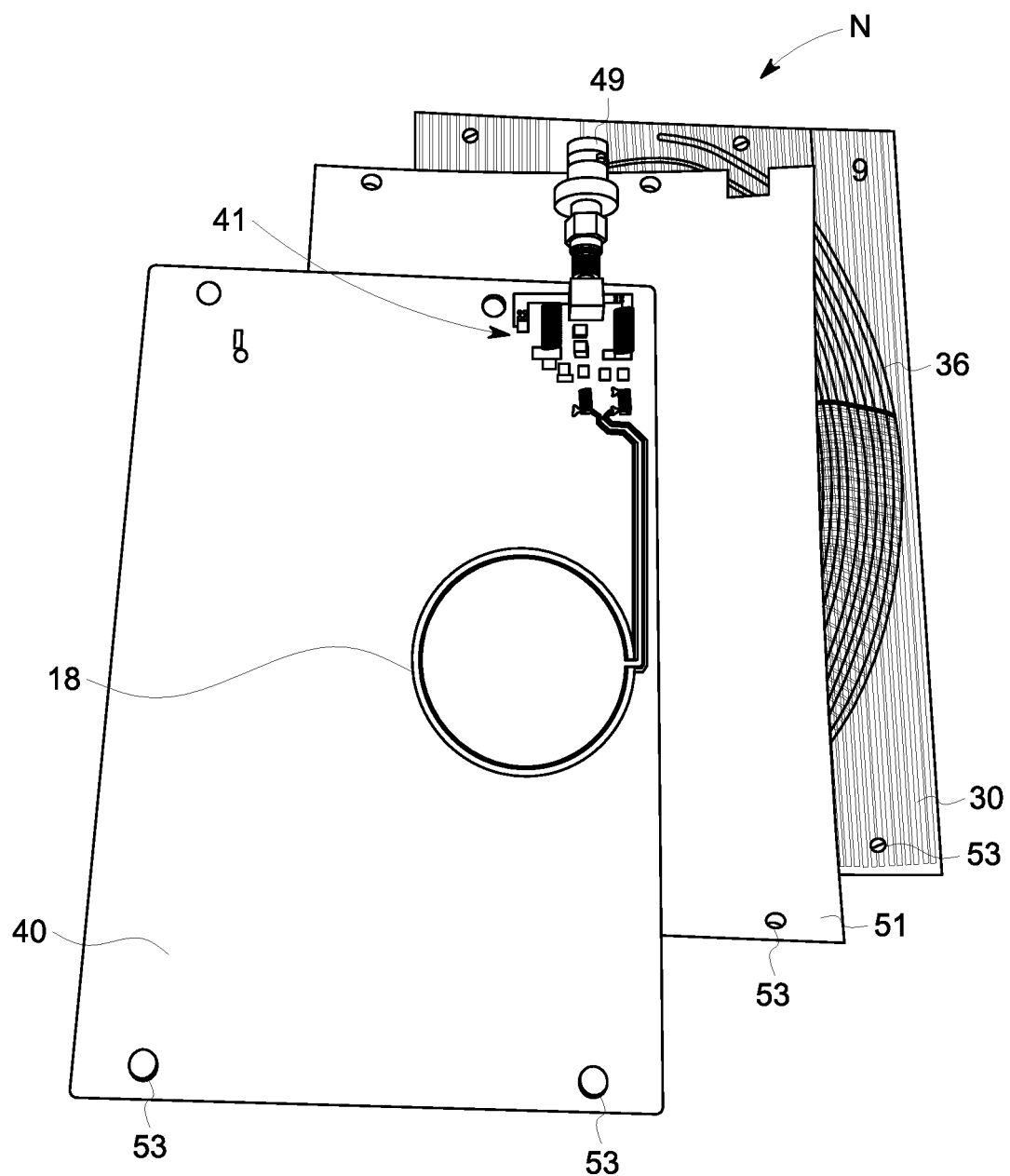
FIG. 5A depicts an exemplary motion sensor according to one embodiment of the present disclosure.
Figure 5B:
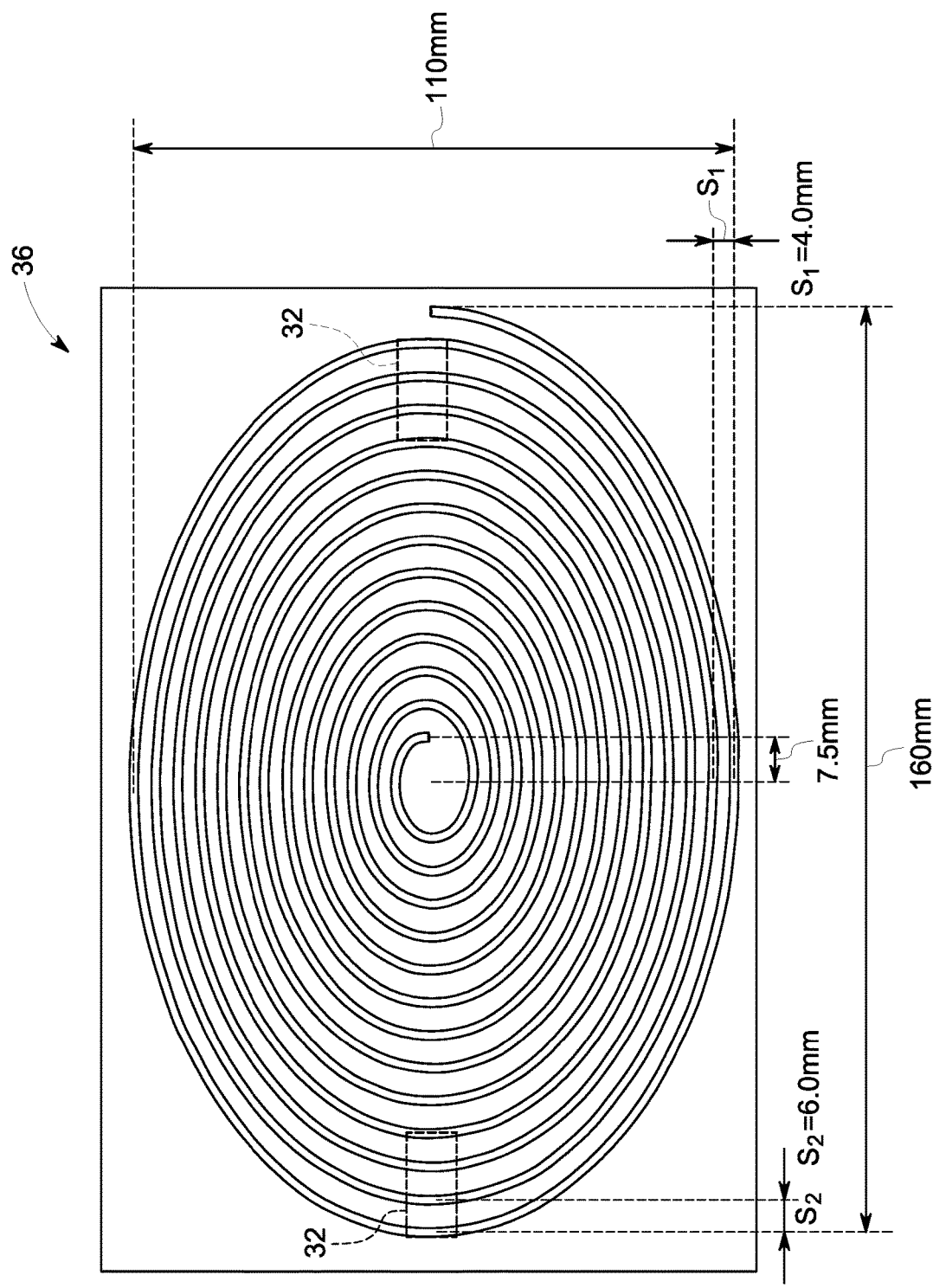
FIG. 5B depicts an exemplary self-resonant spiral coil according to one embodiment of the present disclosure.

FIG. 5A depicts an exemplary sensor 11 assembly comprising a coupling board 40 connectable at a predefined coupling distance to the coil board 30 holding the SRS coil 36 or other resonant coil 16. The coupling board 40 and the coil board 30 are separated by a spacer 51, such as made of foam or other material that does not interfere with the inductive coupling between the coupling loop 18 and the coil 16, 36. For example, the coupling board 40 may be spaced apart from the coil board 30 by, for example, 3/16 inch. The coupling distance, or spacing between the coupling loop 18 and the coil 16, 36 controls the K coupling factor. The coupling board 40 and coil board 30 are connected together, such as via connection points 53, separated by the spacer 51 defining and maintaining the coupling distance.

FIG. 5B depicts an exemplary elliptical SRS coil 36, which is a 13-turn elliptical self-resonant spiral formed by 1 mm copper wire. The spiral is about 110 mm wide and 160 mm long, with a center space of about 7.5 cm. The intra-coil spacing S varies from about 4 mm on the narrow side (the width) to about 6 mm on the longer side (the length). In certain embodiments, a pair of tuning elements 32 may be included to tune the capacitance of the SRS coil 36. The tuning elements are patches of conductive material that, when placed and sized appropriately, provide for a slight adjustment of the total distributed capacitance between the turns of the SRS coil. For example, the tuning elements 32 may be formed of copper or other conductive metal and sized such that the resonant frequency of the coil 36 at its installed location in the table, or for each particular table configuration, is exactly correct. For example, the tuning elements 32 may be located on the opposite side of the coil board 30 from the SRS coil 36.

Figure 6A:
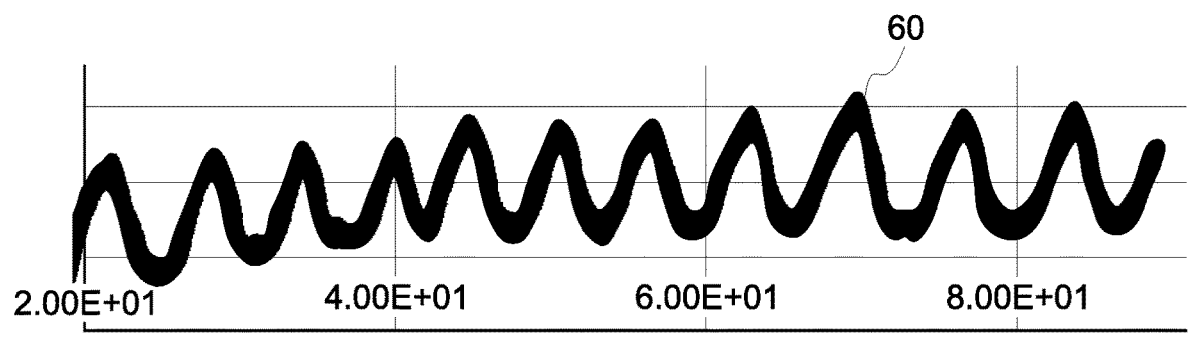
FIG. 6A depicts an exemplary respiration signal generated by a motion sensor according to the present disclosure.
Figure 6B:
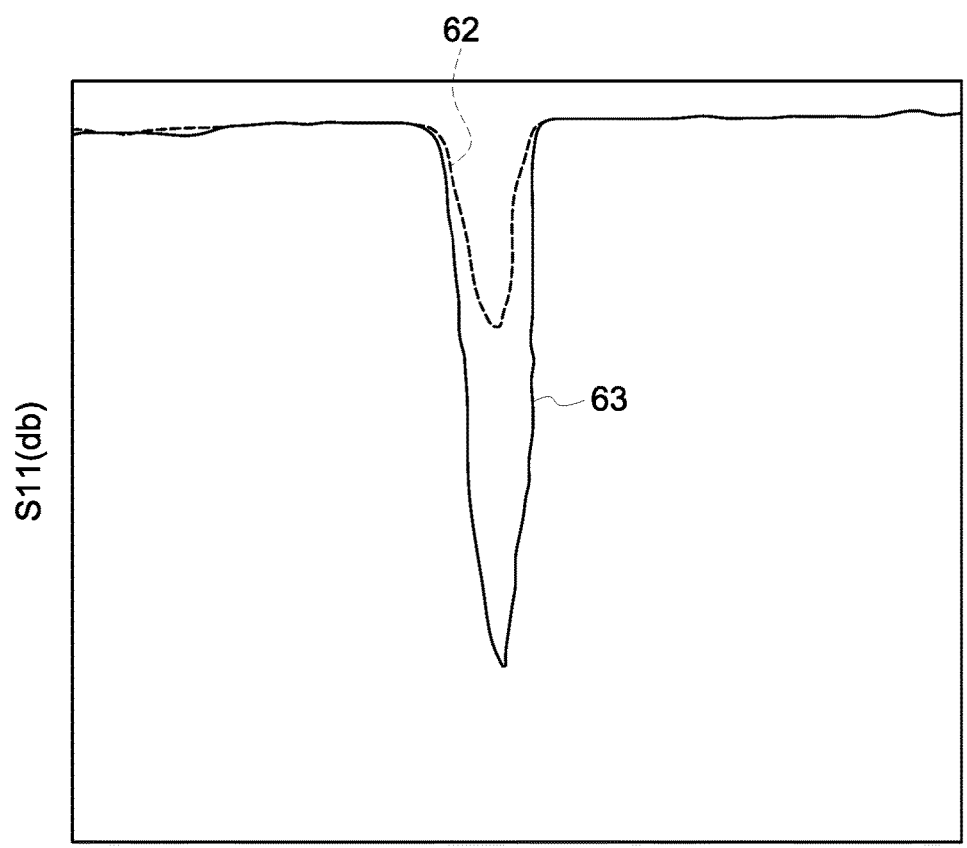
FIG. 6B is a plot of the reflection coefficient (S11) for an exemplary resonant coil in accordance with one embodiment of the disclosure.

FIG. 6A depicts one embodiment of a respiration signal 60 generated by a sensor 11 according to the present disclosure. As can be seen, the respiration signal 60 is generally periodic in nature and represents the patient's respiration motion—i.e. the expansion and contraction of the patient's chest as the patient breathes. The respiration signal 60 can be utilized to control MR image capture, such as via respiratory gating. The respiration signal 60 may be derived based on changes in the reflection coefficient of the coil 16, 36. FIG. 6B is a plot of the reflection coefficient S11 for an exemplary sensor 11.

The reflection coefficient S11 varies due to patient respiration, which is demonstrated in the plot at FIG. 6B. Line 62 shows S11 at the end of inhalation, where the lungs are filled with gas, and line 63 shows S11 at the end of the exhalation cycle. Thus, by tracking S11, the reflection coefficient, the respiration cycle can be tracked.

FIG. 7 is a schematic depiction of a resonant coil 16, 36 and depicts the H-field pattern in a YZ cut plane. The H-field dominates the environment around the resonant coil 16, 36. The depth of the near field 66, where the magnetic field is the strongest, is approximated in meters according to the equation described above. The depth of the near field at 27 MHz will be greater than the near field depth at a higher frequency, such as 240 MHz. The RF magnetic field will have a greater depth of penetration when the source frequency is lower. For example, the near field depth at 240 MHz is about 4 cm, while the depth at 27 MHz increases to about 88 cm. Accordingly, the sensor 11 can be positioned further from the patient at 27 MHz than where a resonant coil at 240 MHz is utilized. The electric field from the coil will be attenuated at a rate of 1/r2. The E-field of the coil will interact with the conductivity of the tissue and may interact with the distributed capacitance used to achieve resonance tuning of the coil. The ampere-turn (At) is the MKS (Meters, Kilograms, Seconds) unit of magnetomotive force (MMF), represented by a direct current of one ampere flowing in a single-turn loop in a vacuum. "Turns" refers to the winding number of an electrical conductor composing an inductor. For example, a current of 2A flowing through a coil of 10 turns produces an MMF of 20 A-t.

By maintaining the same current and increasing the number of loops or turns of the coil, the strength of the magnetic field increases because each loop or turn of the coil sets up its own magnetic field. The magnetic field unites with the fields of the other loops to produce the field around the entire coil, making the total magnetic field stronger. The greater H-field generated by this structure enables the coil to be placed at a greater distance below the patient, within the table, while still producing RF-fields that will interact with the patient tissue. The E-field will be held close to the SRS coil and will weakly couple to the patient. Coil tuning is only weakly affected. In addition, the driven center SRS coil is flanked on both sides with passive elements, such as passive SRS coils that are inductively coupled to the driven SRS coil 36. A larger physical region is excited in the patient than is excited with a single driven element. However, the three loop configuration shown in FIG. 7 is not required and it should be noted that very good results may be obtained using the single loop configuration described and shown herein. Notably, while the passive elements extend the field in the Z direction, the depth in the X-Y plane will be reduced. Moreover, a single loop system is simpler because the tuning interdependencies are eliminated.

Referring to FIGS. 2 and 7, one or more passively coupled elements 26 may be included and located adjacent to the active coil 16, 36 in order to increase the size of the magnetic field along the Z-axis (which extends along the length of the table 171 and head-to-toe with respect to the patient). In FIG. 7, two coupled elements 26a and 26b are positioned on both sides of the resonant coil 16, 36 along the Z-axis, which are inductively coupled into the system. Thereby, a larger physical region is excited in the patient using only a single driven element 16, 36. For example, the coupled elements may be passive SRS coils, and thus do not have a corresponding coupling loop, but are inductively coupled by the magnetic field radiated by the driven SRS coil 36 in the center. In other embodiments exemplified at FIG. 2, only a single coupled element 26 may be passively coupled to each resonant coil 16, thereby extending the magnetic field from the coil 16 in only one direction along the Z-axis.

Accordingly, the disclosed motion sensor system 10 is highly sensitive to respiratory motion, and is more sensitive than smaller coil elements. The disclosed sensor system 10 has applicability to a wide variance of patient population and is reliable and easy to operate, without any additional work required by the clinician performing the MR imaging. The sensor system 10 can be implemented with relatively low cost signal detection circuitry, and may be implemented using existing control systems with minimal additional circuitry, which can be implemented as a "piggy-back" board on an existing PAC. The disclosed motion sensing system 10 can be utilized in existing MR resonance assemblies 140, and are useful with all surface coils and body coils. Accordingly, there is no need for specially designed surface coils in order to integrate the respiration sensing.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A table for a magnetic resonance imaging system, the table comprising:
   a top surface for supporting a patient being imaged;
   a motion sensor for sensing motion of the patient, the motion sensor located below the top surface and including:
   a self-resonant spiral (SRS) coil;
   a single coupling loop inductively coupled to the SRS coil and configured to:
   generate a drive RF signal to excite the SRS coil to radiate a magnetic field having a predefined resonant frequency; and
   receive a reflection RF signal from the SRS coil;
   wherein the motion sensor is located such that at least a portion of a torso of the patient being imaged is within the magnetic field; and
   a controller configured to detect patient motion based on the reflection RF signal.

2. The table of claim 1, wherein the motion sensor is configured to sense motion of the patient due to respiration and wherein the controller is configured to generate a respiration signal based on changes in the reflection RF signal due to the patient's respiration.

3. The table of claim 2, wherein the respiration signal is determined based on changes in a reflection coefficient of the SRS coil over time.

4. The table of claim 1, wherein the table further includes at least one phased-array (PA) coil, and wherein the at least one PA coil is between the top surface of the table and the SRS coil.

5. The table of claim 1, wherein the predefined resonant frequency is less than a Larmor frequency.

6. The table of claim 1, wherein the predefined resonant frequency is between 26.957 MHz and 27.283 MHz.

7. The table of claim 1, wherein the predefined resonant frequency is with an Industrial, Scientific, and Medical (ISM) band.

8. The table of claim 1, wherein the SRS coil is an elliptical spiral having between 10 and 15 turns.

9. The table of claim 1, further comprising a pair of tuning elements capacitively coupled to the SRS coil, wherein a size of the tuning elements is selected to calibrate the SRS coil to resonate at the predefined resonant frequency.

10. The table of claim 1, further comprising at least one passively coupled element adjacent to the SRS coil and inductively coupled thereto so as to extend the magnetic field along a length of the table.

11. The table of claim 1, wherein the table further comprises a second motion sensor including:
    a second SRS coil;
    a second coupling loop coupled to the second SRS coil, wherein the second coupling loop is configured to generate a drive RF signal to excite the SRS coil to radiate a magnetic field having the predefined resonant frequency, and to receive a reflection RF signal from the second SRS coil;
    wherein the SRS coil and the coupling loop are located toward a front end of the table and the second SRS coil and the second coupling loop are located toward a back end of the table; and
    a switch configured to alternately connect one of the coupling loop and the second coupling loop to the controller.

12. A magnetic resonance imaging system comprising:
- a bore;
- a table configured to support a patient being imaged and movable to move the patient in and out of the bore;
- a motion sensor for sensing motion of the patient, the motion sensor including:
- a self-resonant spiral (SRS) coil excited by a drive signal to radiate a magnetic field having a predefined resonant frequency;
- a driver-receiver coupled to the SRS coil and configured to generate the drive signal to excite the SRS coil and to receive an RF signal from the SRS coil;
- wherein the motion sensor is located such that at least a portion of a patient's torso is within the magnetic field while the patient is being imaged in the bore; and
- a controller configured to detect patient motion based on changes in the RF signal.

13. The system of claim 12, wherein the motion sensor is located below a top surface of the table.

14. The system of claim 12, wherein the driver-receiver is a coupling loop inductively coupled to the SRS coil, wherein the coupling loop is configured to generate the drive signal to excite the SRS coil to radiate the magnetic field having the predefined resonant frequency, and wherein the RF signal received from the SRS coil is a reflection RF signal; and
- wherein the motion sensor is configured to sense motion of the patient due to respiration and wherein the controller is configured to generate a respiration signal based on the changes in the reflection RF signal due to the patient's respiration.

15. The system of claim 14, wherein the respiration signal is formatted for use in triggering MR image data acquisition.

16. The system of claim 14, wherein the respiration signal is determined based on changes in a reflection coefficient of the SRS coil over time.

17. A magnetic resonance imaging system comprising:
- a bore;
- a table having a top surface that supports a patient being imaged and movable to move the patient in and out of the bore;
- a motion sensor system located below the top surface of the table and configured to sense motion of the patient due to respiration, the motion sensor system including:
- a first resonant coil located toward a front end of the table;
- a first coupling loop coupled to the first resonant coil, wherein the first coupling loop is configured to generate a drive RF signal to excite the first resonant coil to radiate a magnetic field having a predefined resonant frequency, and to receive a reflection RF signal from the first resonant coil;
- a second resonant coil located toward a back end of the table;
- a second coupling loop coupled to the second resonant coil, wherein the second coupling loop is configured to generate a drive RF signal to excite the second resonant coil to radiate a magnetic field having the predetermined resonant frequency, and to receive a reflection RF signal from the second resonant coil;
- a switch configured to alternately connect one of the first coupling loop and the second coupling loop to a controller;
- a controller configured to generate a respiratory signal based on changes in the reflection RF signal due to respiration.

18. The system of claim 17, wherein the respiratory signal is determined based on a change in a reflection coefficient of the connected one of the first resonant coil or the second resonant coil over time, and wherein the respiration signal is formatted for use in triggering MR image data acquisition.

19. The system of claim 17, further comprising at least one phased-array (PA) coil located between the top surface of the table and the first resonant coil and the second resonant coil.

20. The system of claim 17, wherein each of the first resonant coil and the second resonant coil are an elliptical self-resonant spiral (SRS) coil.

21. The system of claim 17, wherein the predetermined resonant frequency is between 26.957 MHz and 27.283 MHz, between 40.66 MHz and 40.7 MHz, or between 13.553 MHz and 13.567 MHz.

22. The system of claim 17, further comprising at least one passively coupled element adjacent to one of the first resonant coil and the second resonant coil and passively coupled thereto, wherein the at least one passive coupled element extends the magnetic field of radiated by the respective coil along the length of the table.

* * * * *